United States Patent
Yang et al.

(10) Patent No.: US 8,088,301 B2
(45) Date of Patent: Jan. 3, 2012

(54) EPOXY COMPOUND FOR LIQUID CRYSTAL PHOTO-ALIGNMENT AGENT, LIQUID CRYSTAL PHOTO-ALIGNMENT AGENT, AND LIQUID CRYSTAL PHOTO-ALIGNMENT FILM

(75) Inventors: Jae-Deuk Yang, Uiwang-si (KR);
Dong-Seon Uh, Uiwang-si (KR);
Tae-Hyoung Kwak, Uiwang-si (KR);
Hyo-Ju Seo, Uiwang-si (KR)

(73) Assignee: Cheil Industries Inc., Gumi-si (KR)

( * ) Notice: Subject to any disclaimer, the term of this patent is extended or adjusted under 35 U.S.C. 154(b) by 233 days.

(21) Appl. No.: 12/632,870

(22) Filed: Dec. 8, 2009

(65) Prior Publication Data

US 2010/0155661 A1    Jun. 24, 2010

(30) Foreign Application Priority Data

Dec. 23, 2008 (KR) .......... 10-2008-0132404
Dec. 4, 2009 (KR) .......... 10-2009-0119898

(51) Int. Cl.
*C09K 19/56* (2006.01)
*C07D 303/12* (2006.01)
*C08K 5/1515* (2006.01)

(52) U.S. Cl. ............. 252/299.4; 428/1.2; 428/1.25; 428/1.26; 549/557; 524/114

(58) Field of Classification Search ............. 252/299.01, 252/299.4; 428/1.2, 1.25, 1.26; 549/557; 524/114; 525/422

See application file for complete search history.

(56) References Cited

U.S. PATENT DOCUMENTS

| 5,218,074 A | 6/1993 | Nordmann et al. |
| 2007/0154658 A1* | 7/2007 | Kang et al. .......... 428/1.25 |
| 2008/0293888 A1 | 11/2008 | Bachels et al. |
| 2009/0146105 A1* | 6/2009 | Oh et al. .......... 252/299.61 |

FOREIGN PATENT DOCUMENTS

| DE | 4423044 A1 | 1/1996 |
| EP | 0477666 A1 | 4/1992 |
| JP | 2008-009419 | 1/2008 |
| JP | 2008-181102 | 8/2008 |
| WO | 2008/135131 A1 | 11/2008 |

* cited by examiner

*Primary Examiner* — Shean Wu
(74) *Attorney, Agent, or Firm* — Summa, Additon & Ashe, P.A.

(57) ABSTRACT

Disclosed is an epoxy compound for a liquid crystal photo-alignment agent, a liquid crystal photo-alignment agent, and a liquid crystal photo-alignment film. The epoxy compound is represented by the following Chemical Formula 1.

[Chemical Formula 1]

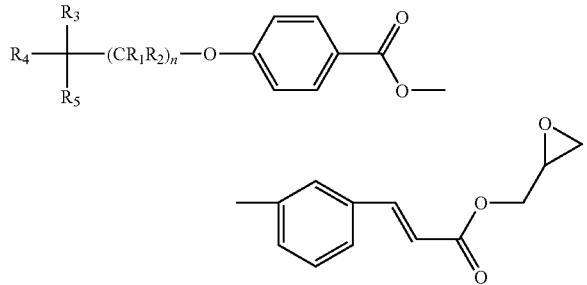

In the above Chemical Formula 1, each substituent is the same as defined in the specification.

Since the epoxy compound according to an embodiment of the present invention may be prepared through a simple manufacturing process, it is possible to provide a liquid crystal photo-alignment agent and a liquid crystal photo-alignment film that are economical and have excellent substrate printability and reliability, and superb photoelectric characteristics.

9 Claims, 2 Drawing Sheets

EPOXY COMPOUND FOR LIQUID CRYSTAL PHOTO-ALIGNMENT AGENT, LIQUID CRYSTAL PHOTO-ALIGNMENT AGENT, AND LIQUID CRYSTAL PHOTO-ALIGNMENT FILM

CROSS-REFERENCE TO RELATED APPLICATION

This application claims priority to and the benefit of Korean Patent Application Nos. 10-2008-0132404 and 10-2009-0119898 filed in the Korean Intellectual Property Office on Dec. 23, 2008 and Dec. 4, 2009, the entire disclosure of which is incorporated herein by reference.

FIELD OF THE INVENTION

The present invention relates to an epoxy compound for a liquid crystal photo-alignment agent, a liquid crystal photo-alignment agent, and a liquid crystal photo-alignment film.

BACKGROUND OF THE INVENTION

A liquid crystal display (LCD) includes a liquid crystal alignment film. The liquid crystal alignment film is mainly made of polymer materials. The liquid crystal alignment film directs the alignment of liquid crystal molecules. When the liquid crystal molecules are moved by the influence of an electric field to display an image, the liquid crystal alignment film allows the liquid crystal molecules to be oriented in a predetermined direction. Generally, it is necessary to uniformly align the liquid crystal molecules in order to provide uniform luminance and a high contrast ratio to the liquid crystal device.

The conventional method of aligning liquid crystal molecules includes coating a polymer film such as a polyimide on a substrate made of a material such as glass, and rubbing the surface of the substrate with a fiber such as nylon or polyester in a certain direction. However, the rubbing method may cause serious problems when fabricating a liquid crystal panel due to fine dust or electrostatic discharge (ESD) that may be generated while rubbing the polymer film with the fiber.

In order to solve the problems of the rubbing method, a photo-radiation method has recently been researched to induce anisotropy to the polymer film by irradiating light on the membrane so as to align the liquid crystal molecules.

As polymer film materials for the photo-alignment method, polymers having photo-functional groups such as azobenzene, cumarine, chalcone, and cinnamate have been suggested. To prepare the polymers with photo-functional groups, dinitro-based compounds with excellent stability should be used. However, the dinitro-based compounds include double bonds which can degrade where photo-crosslinking occurs due to polarized photo-radiation in the course of preparing the polymers with photo-functional groups. Thus, it is difficult to use the dinitro-based compounds to prepare a photo-alignment agent. Also, the process for preparing the polymers with photo-functional groups is too complicated to be economically efficient.

SUMMARY OF THE INVENTION

An exemplary embodiment of the present invention provides an epoxy compound for a liquid crystal alignment agent that can be prepared through a simple process and used for preparing a photo-alignment agent with excellent luminance.

Another embodiment of the present invention provides a liquid crystal photo-alignment agent including the epoxy compound and having excellent luminance.

Yet another embodiment of the present invention provides a liquid crystal photo-alignment film using the liquid crystal photo-alignment agent and having excellent luminance.

The embodiments of the present invention are not limited to the above technical purposes, and a person of ordinary skill in the art can understand other technical purposes.

An embodiment of the present invention provides an epoxy compound for liquid crystal photo-alignment agent represented by the following Chemical Formula 1.

[Chemical Formula 1]

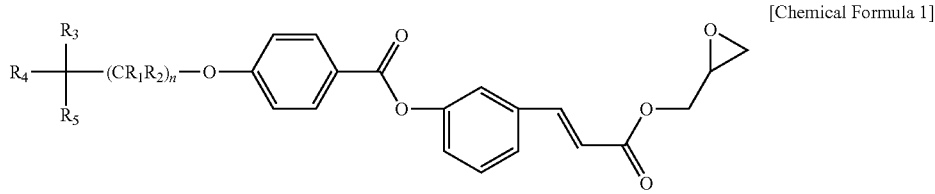

In the above Chemical Formula 1,
each $R_1$ and $R_2$ is independently hydrogen or substituted or unsubstituted alkyl,
$R_3$, $R_4$, and $R_5$ are independently hydrogen, halogen, or substituted or unsubstituted alkyl, and
n ranges from 1 to 20.

Another embodiment of the present invention provides a liquid crystal photo-alignment agent including the epoxy compound represented by Chemical Formula 1, and a polymer comprising a polymer of polyamic acid, a polyimide polymer, or a combination thereof.

Yet another embodiment of the present invention provides a liquid crystal photo-alignment film fabricated by coating a substrate with the liquid crystal photo-alignment agent.

Further embodiments of the present invention will be described in detail.

The liquid crystal photo-alignment agent prepared according to an embodiment of the present invention is used to fabricate a liquid crystal photo-alignment film with excellent substrate printing performance, reliability, and superb photo-electric characteristics.

DETAILED DESCRIPTION OF THE INVENTION

Figure 1:
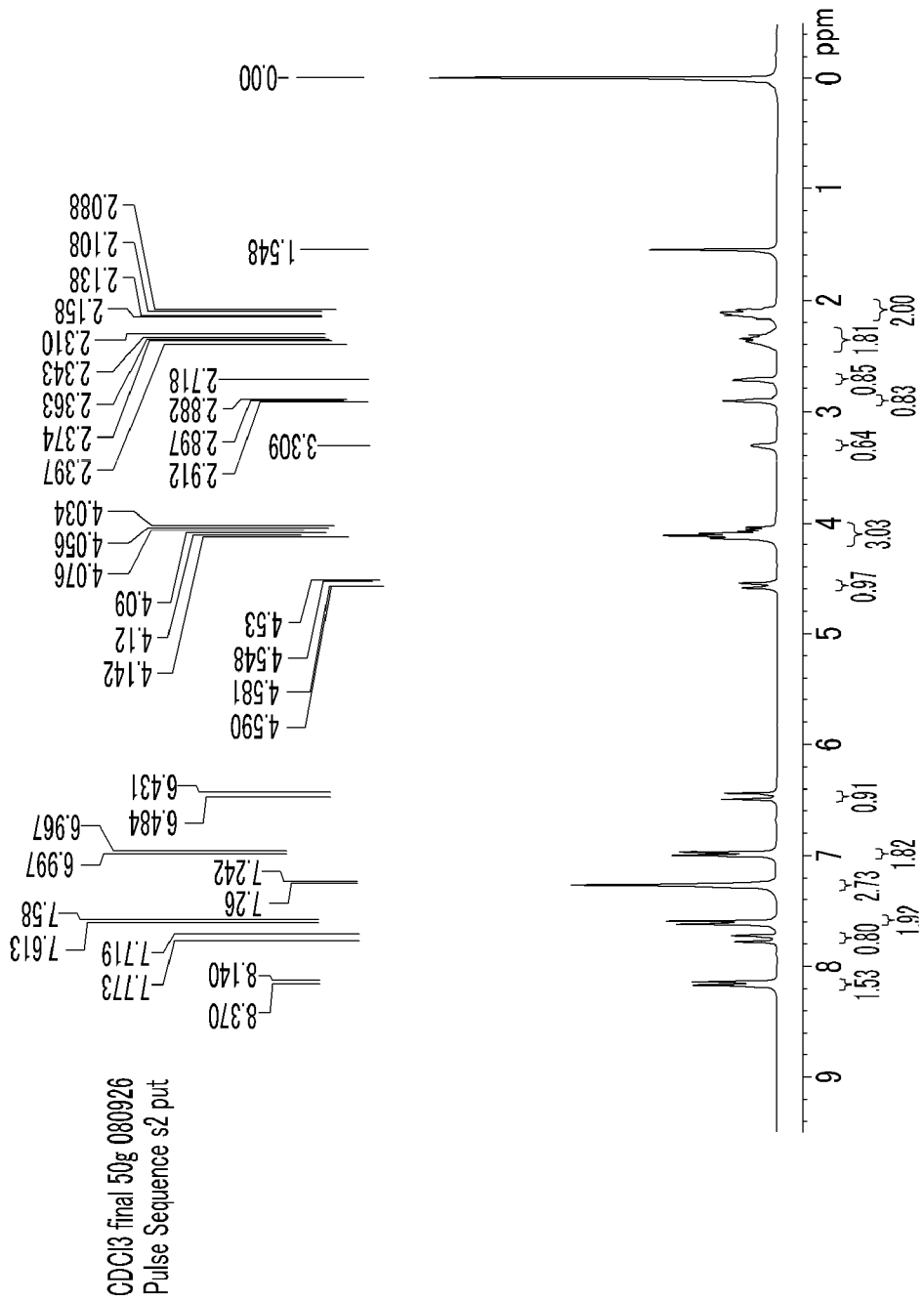
FIG. 1 is a graph showing results of nuclear magnetic resonance (NMR) spectroscopy of an epoxy compound prepared according to Example 1 of the present invention.

The present invention now will be described more fully hereinafter in the following detailed description of the invention, in which some, but not all embodiments of the invention are described. Indeed, this invention may be embodied in many different forms and should not be construed as limited to the embodiments set forth herein; rather, these embodiments are provided so that this disclosure will satisfy applicable legal requirements.

As used herein, when a specific definition is not otherwise provided, the term "alkyl" refers to a C1-C30 alkyl, the term "cycloalkyl" refers to a C3-C30 cycloalkyl, the term "alkylene" refers to a C1-C6 alkylene, the term "cycloalkylene" refers to a C3-C30 cycloalkylene, the term "heterocycloalkylene" refers to a C2-C30 heterocycloalkylene, the term "aryl" refers to a C6-C30 aryl, the term "heteroaryl" refers to a C2-C30 heteroaryl, the term "arylene" refers to a C2-C20 arylene, the term "heteroarylene" refers to a C2-C30 heteroarylene, the term "alkylaryl" refers to a C7-C30 alkylaryl, and the term "halogen" refers to F, Cl, Br, or I.

As used herein, when a specific definition is not otherwise provided, the terms substituted alkyl, substituted alkylene, substituted cycloalkylene, substituted heterocycloalkylene, substituted aryl, substituted arylene, substituted heteroaryl, substituted heteroarylene, substituted pyrimidinyl, substituted pyridinyl, substituted thiophenyl, substituted furanyl, substituted naphthyl, and substituted phenyl respectively refer to an alkyl, an alkylene, a cycloalkylene, a heterocycloalkylene, an aryl, an arylene, a heteroaryl, a heteroarylene, a pyrimidinyl, a pyridinyl, a thiophenyl, a furanyl, a naphthyl, and a phenyl substituted with one or more halogen, C1 to C30 alkyl, C1 to C30 haloalkyl, C6 to C30 aryl, C2 to C30 heteroaryl, C1 to C20 alkoxy, or a combination thereof.

As used herein, when a specific definition is not otherwise provided, the terms "a heterocycloalkylene", "a heteroaryl", and "a heteroarylene" refer to a cycloalkylene, an aryl, and an arylene in which carbon atoms in a ring are substituted with one to three heteroatoms selected from N, O, S, Si, and P atoms, and combinations thereof, with the remaining atoms in the ring being carbon atoms.

An epoxy compound for a liquid crystal photo-alignment agent according to an embodiment of the present invention may be represented by the following Chemical Formula 1.

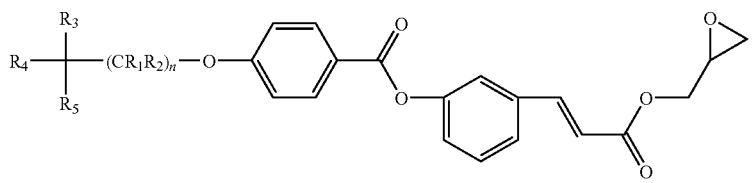

[Chemical Formula 1]

In the above Chemical Formula 1, each $R_1$ and $R_2$ is independently hydrogen or substituted or unsubstituted alkyl, $R_3$, $R_4$, and $R_5$ are independently hydrogen, halogen, or substituted or unsubstituted alkyl, and n ranges from 1 to 20.

In one embodiment of the present invention, each $R_1$ and $R_2$ is independently hydrogen, $R_3$, $R_4$, and $R_5$ are independently halogen, and n is 2, 3, or 4.

Examples of the epoxy compound include at least one compound represented by the following Chemical Formulae 2 and 3.

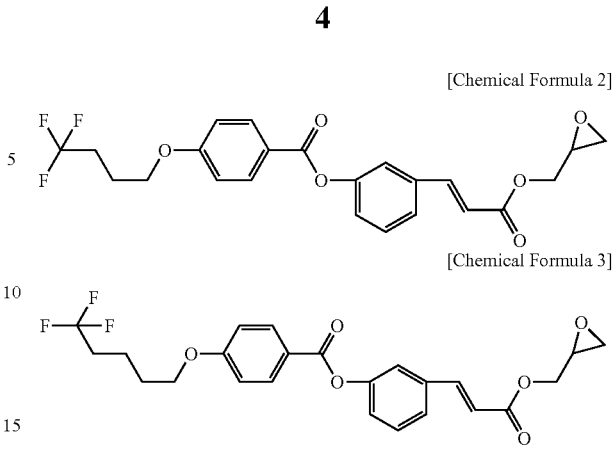

[Chemical Formula 2]

[Chemical Formula 3]

The epoxy compound may be prepared through a simple preparation process, and when the epoxy compound is used for a liquid crystal photo-alignment agent, it reacts with COOH of polyamic acid to thereby decrease the number of COOH groups that may exist in the liquid crystal photo-alignment agent. Therefore, it is possible to prevent after-images and improve luminance.

The epoxy compound may be prepared through the following process.

A compound represented by Chemical Formula 1-A and a compound represented by Chemical Formula 1-B are reacted with each other in an organic solvent.

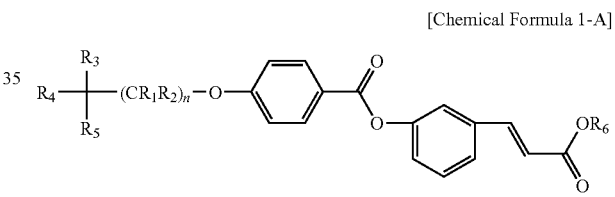

[Chemical Formula 1-A]

In the above Chemical Formula 1-A, $R_1$, $R_2$, $R_3$, $R_4$, and $R_5$ are the same as defined above, and $R_6$ is hydrogen.

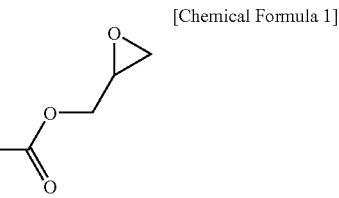

[Chemical Formula 1-B]

In the above Chemical Formula 1-B, $R_7$ is hydrogen.

Exemplary organic solvents include without limitation methylene chloride, tetrahydrofuran, diethylether, ethylene chloride, and the like, and combinations including two or more thereof.

The reaction molar ratio of the chemical compound of Chemical Formula 1-A to the chemical compound of Chemical Formula 1-B may range from about 1:1.2 to about 1:2.

Also, the reaction may be performed in the presence of a nitrogen-containing compound. Exemplary nitrogen-containing compounds include without limitation 1-ethyl-3-(3-dimethylaminopropyl)carbodiimide, 3-dimethylamino propylamine, and the like and combinations thereof.

After the reaction is complete, the reaction product can be rinsed, filtrated, and dried using generally known processes.

According to another embodiment of the present invention, a liquid crystal photo-alignment agent includes an epoxy compound represented by Chemical Formula 1, and a polymer comprising a polymer of polyamic acid, a polyimide polymer, or a combination thereof.

Hereafter, each element will be described in detail.

(A) Epoxy Compound

The epoxy compound may be represented by Chemical Formula 1. A liquid crystal photo-alignment agent including the epoxy compound in addition to a polymer selected from a polymer of polyamic acid, a polyimide polymer, or a combination thereof can have excellent luminance and may prevent after-images.

The liquid crystal photo-alignment agent can include the epoxy compound according to the embodiment of the present invention in an amount ranging from about 0.01 to about 60 parts by weight based on about 100 parts by weight of solids, which are the epoxy compound and the polymer in the liquid crystal photo-alignment agent. In one embodiment, the amount of the epoxy compound in liquid crystal photo-alignment agent may range from about 0.01 to about 40 parts by weight. When the content of the epoxy compound is within the above ranges, the liquid crystal photo-alignment agent can properly cause a photo-polymerization reaction without deteriorated printability and flatness when it is applied to a substrate.

Non-limiting examples of the epoxy compound may be at least one of the chemical compounds represented by the following Chemical Formulae 2 and 3.

[Chemical Formula 2]

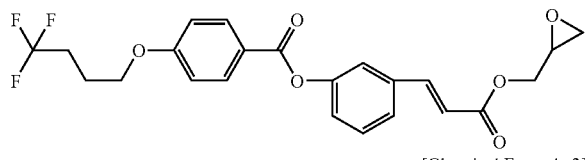

[Chemical Formula 3]

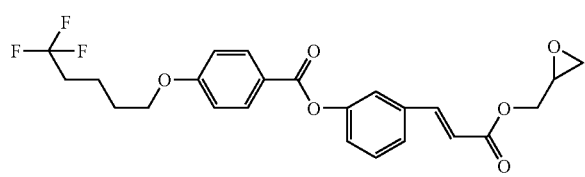

(B) Polymer

The polymer includes a polymer of polyamic acid, a polyimide polymer, or a combination thereof. When the polyamic acid polymer and polyimide polymer are used in combination with one another, they can be mixed at a ratio of polyamic acid:polyimide polymer of about 1 to about 99 wt % to about 99 to about 1 wt %.

(B-1) Polyamic Acid

The polyamic acid used for a liquid crystal photo-alignment agent may be any one synthesized from an acid dianhydride and a diamine.

The acid dianhydride may be an aliphatic cyclic acid dianhydride, an aromatic acid dianhydride, or a combination thereof. The diamine may be an aromatic diamine, a functional diamine, or a combination of an aromatic diamine and a functional diamine. When a mixture of an aromatic diamine and a functional diamine is used, it may be easier to control the pretilt angle of liquid crystal molecules in a liquid crystal photo-alignment film, and as a result, the liquid crystal photo-alignment film can have excellent alignment characteristics.

The acid dianhydride and diamine may be co-polymerized using any method known in the art for preparing a polyamic acid polymer, and the skilled artisan will understand and appreciate how to conduct such a reaction without undue experimentation.

A non-limiting example of the polyamic acid according to an embodiment of the present invention may be represented by the following Chemical Formula 5.

[Chemical Formula 5]

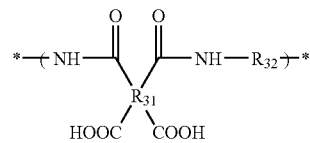

In the above Chemical Formula 5, $R_{31}$ is a quadrivalent organic group derived from an aliphatic cyclic acid dianhydride or an aromatic acid dianhydride, and $R_{32}$ is a divalent organic group derived from a diamine.

(B-1-1) Acid Dianhydride (B-1-1-1) Aliphatic Cyclic Acid Dianhydride

Non-limiting examples of the aliphatic cyclic acid dianhydride include 1,2,3,4-cyclobutanetetracarboxylic acid dianhydride (CBDA), 5-(2,5-dioxotetrahydrofuryl)-3-methylcyclohexene-1,2-dicarboxylic acid anhydride (DOCDA), bicyclooctene-2,3,5,6-tetracarboxylic acid dianhydride (BODA), 1,2,3,4-cyclopentanetetracarboxylic acid dianhydride (CPDA), 1,2,4,5-cyclohexanetetracarboxylic acid dianhydride (CHDA), 1,2,4-tricarboxyl-3-methylcarboxyl cyclopentane dianhydride, 1,2,3,4-tetracarboxyl cyclopentane dianhydride, 4,10-dioxa-tricyclo[6.3.1.02,7]dodecane-3,5,9,11-tetraone, and the like, and combinations thereof.

A quadrivalent organic group derived from the aliphatic cyclic acid dianhydride may have a structure of at least one or a combination of one or more of the chemical compounds represented by the following Chemical Formulae 7 to 11.

[Chemical Formula 7]

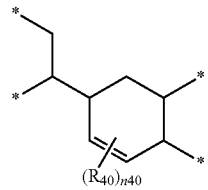

[Chemical Formula 8]

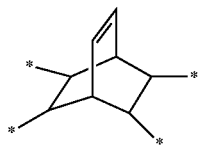

[Chemical Formula 9]

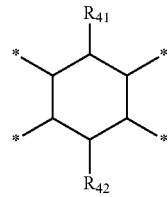

[Chemical Formula 10]

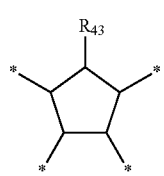

[Chemical Formula 11]

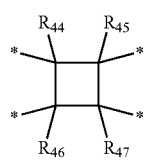

In the above Chemical Formulae 7 to 11, each $R_{40}$ is substituted or unsubstituted C1 to C20 alkyl, substituted or unsubstituted C6 to C30 aryl, or substituted or unsubstituted C2 to C30 heteroaryl, and $n_{40}$ is an integer ranging from 0 to 3, and $R_{41}$ to $R_{47}$ are independently hydrogen, substituted or unsubstituted C1 to C20 alkyl, substituted or unsubstituted C6 to C30 aryl, or substituted or unsubstituted C2 to C30 heteroaryl.

(B-1-1-2) Aromatic Acid Dianhydride

Non-limiting examples of the aromatic acid dianhydride include pyromellitic acid dianhydride (PMDA), biphthalic acid dianhydride (BPDA), oxydiphthalic acid dianhydride (ODPA), benzophenone tetracarboxylic acid dianhydride (BTDA), hexafluoroisopropylidene diphthalic acid dianhydride (6-FDA), and the like, and combinations thereof.

A quadrivalent organic group derived from the aromatic acid dianhydride may have a structure of at least one or a combination of one or more of chemical compounds represented by the following Chemical Formulae 12 and 13.

[Chemical Formula 12]

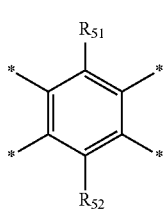

[Chemical Formula 13]

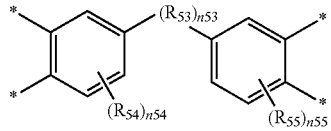

In the above Chemical Formulae 12 and 13, $R_{51}$ and $R_{52}$ are independently hydrogen, substituted or unsubstituted C1 to C20 alkyl, substituted or unsubstituted C6 to C30 aryl, or substituted or unsubstituted C2 to C30 heteroaryl, each $R_{54}$ and $R_{55}$ is independently substituted or unsubstituted C1 to C20 alkyl, substituted or unsubstituted C6 to C30 aryl, or substituted or unsubstituted C2 to C30 heteroaryl, $n_{54}$ and $n_{55}$ are independently integers ranging from 0 to 3, $R_{53}$ is O, CO, substituted or unsubstituted alkylene such as —$C(CF_3)_2$—), substituted or unsubstituted cycloalkylene, or substituted or unsubstituted heterocycloalkylene, and $n_53$ is an integer of 0 or 1.

(B-1-2) Diamine (B-1-2-1) Aromatic Diamine

Non-limiting examples of the aromatic diamine include paraphenylenediamine (p-PDA), 4,4-methylene dianiline (MDA), 2,2'-dimethyl benzidine (DMBZ), 3,3'-dimethyl benzidine, 4,4-oxydianiline (ODA), metabisaminophenoxydiphenylsulfone (m-BAPS), parabisaminophenoxydiphenylsulfone (p-BAPS), 2,2-bis[(aminophenoxy)phenyl]propane (BAPP), 2,2-bisaminophenoxyphenylhexafluoropropane (HF-BAPP), 1,4-diamino-2-methoxybenzene, and the like, and combinations thereof.

A bivalent organic group derived from the aromatic diamine may have a structure of at least one or a combination of one or more of chemical compounds represented by the following Chemical Formulae 14 to 16.

[Chemical Formula 14]

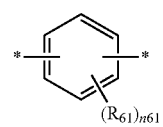

[Chemical Formula 15]

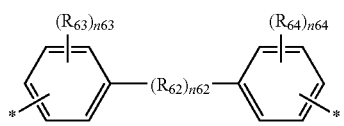

[Chemical Formula 16]

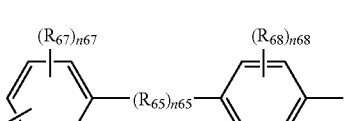

In the above Chemical Formulae 14 to 16, each $R_{61}$, $R_{63}$, $R_{64}$, and $R_{67}$ to $R_{69}$ is independently substituted or unsubstituted C1 to C20 alkyl, substituted or unsubstituted C6 to C30 aryl, or substituted or unsubstituted C2 to C30 heteroaryl, or alkyl, aryl, or heteroaryl including at least one of —O—, —COO—, —CONH—, or —OCO—, $R_{62}$, $R_{65}$, and $R_{66}$ are independently —O—, —$SO_2$—, or $C(R')(R'')$ such as —$C(CF_3)_2$— where R' and R'' are independently hydrogen or substituted or unsubstituted C1 to C6 alkyl, $n_{61}$, $n_{63}$, $n_{64}$, and $n_{67}$ to $n_{69}$ are independently integers ranging from 0 to 4, and $n_{62}$, $n_{65}$, and $n_{66}$ are independently integers of 0 or 1.

(B-1-2-2) Functional Diamine

Any one of chemical compounds represented by the following Chemical Formulae 17 to 19 or a combination thereof may be used as the functional diamine. When a mixture of a functional diamine and an aromatic diamine is used, a part of the prepared polyamic acid includes a functional group derived from the aromatic diamine, and another part of the prepared polyamic acid includes a bivalent organic group derived from the functional diamine.

[Chemical Formula 17]

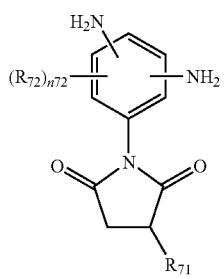

In the above Chemical Formula 17, $R_{71}$ is hydrogen, substituted or unsubstituted C1 to C20 alkyl, substituted or unsubstituted C6 to C30 aryl, or substituted or unsubstituted C2 to C30 heteroaryl, each $R_{72}$ is substituted or unsubstituted C1 to C20 alkyl, substituted or unsubstituted C6 to C30 aryl, or substituted or unsubstituted C2 to C30 heteroaryl, and $n_{72}$ is an integer ranging from 0 to 3.

[Chemical Formula 18]

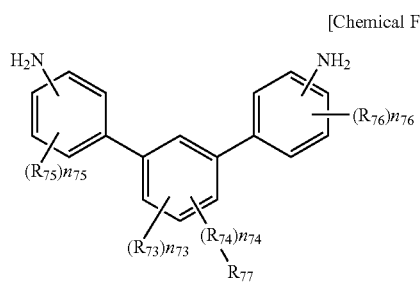

In the above Chemical Formula 18, each $R_{73}$, $R_{75}$, and $R_{76}$ is independently substituted or unsubstituted C1 to C20 alkyl, substituted or unsubstituted C6 to C30 aryl, or substituted or unsubstituted C2 to C30 heteroaryl, $R_{74}$ is —O—, —COO—, —CONH—, —OCO—, or substituted or unsubstituted C1 to C10 alkylene, $R_{77}$ is hydrogen, substituted or unsubstituted C1 to C20 alkyl, substituted or unsubstituted C6 to C30 aryl, or substituted or unsubstituted C2 to C30 heteroaryl, or alkyl, aryl, or heteroaryl including at least one of —O—, —COO—, —CONH—, or —OCO—, $n_{73}$ is an integer of 0 to 3, $n_{75}$ and $n_{76}$ are independently integers ranging from 0 to 4, and $n_{74}$ is an integer of 0 or 1.

[Chemical Formula 19]

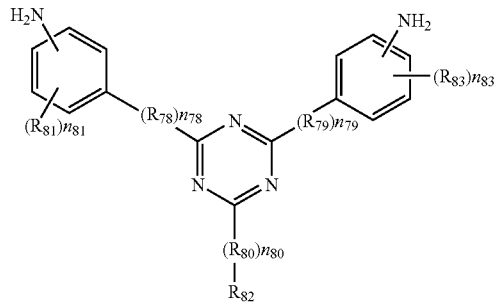

In the above Chemical Formula 19, each $R_{81}$ and $R_{83}$ is independently substituted or unsubstituted C1 to C20 alkyl, substituted or unsubstituted C6 to C30 aryl, or substituted or unsubstituted C2 to C30 heteroaryl, $R_{82}$ is hydrogen, substituted or unsubstituted C1 to C20 alkyl, substituted or unsubstituted C6 to C30 aryl, or substituted or unsubstituted C2 to C30 heteroaryl, $R_{78}$ and $R_{79}$ are independently —O— or —COO—, $R_{80}$ is —O—, —COO—, —CONH—, or —OCO—, $n_{81}$ and $n_{83}$ are independently integers ranging from 0 to 4, and $n_{78}$ to $n_{80}$ are independently integers of 0 or 1.

(B-2) Polyimide Polymer

The polyimide polymer may be any polyimide polymer used for liquid crystal photo-polymers and polyimide photo-polymers.

The polyimide polymer may be prepared by imidizing the polyamic acid represented by Chemical Formula 1, or it may be synthesized from at least one of a photo-diamine and an acid dianhydride. Methods of preparing a polyimide polymer by imidizing polyamic acid and methods of preparing a polyimide polymer from a photo-diamine and acid dianhydride are widely known to those skilled in the art to which the present invention pertains, and accordingly detailed descriptions thereof will not be provided herein.

A non-limiting example of the polyimide polymer according to an embodiment of the present invention includes a chemical compound represented by the following Chemical Formula 6.

[Chemical Formula 6]

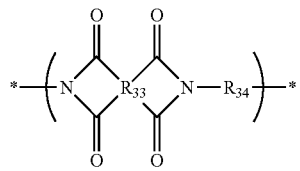

In the above Chemical Formula 6, $R_{33}$ is an quadrivalent organic group derived from an aliphatic cyclic acid dianhydride or an aromatic acid dianhydride, and $R_{34}$ is a divalent organic group derived from an aromatic diamine (the details of which are the same as those of the aromatic diamine discussed herein with regard to the polyamic acid) or a divalent organic group derived from a cumarin-based photodiamine, a chalcone-based photodiamine, or a cinnamate-based photodiamine.

(B-2-1) Acid Dianhydride

The acid dianhydride used for the preparation of the polyimide polymer may be an aliphatic cyclic acid dianhydride, an aromatic acid dianhydride, or a combination thereof. Details thereof are the same as those of the acid dianhydride discussed herein with regard to the polyamic acid.

(B-2-2) Photo-Diamine

The photo-diamine used for the preparation of the polyimide polymer may be a cinnamate-based photo-diamine, a chalcone-based photo-diamine, a coumarin-based photo-diamine, or a combination thereof.

In an embodiment of the present invention, the cinnamate-based photo-diamine may be a chemical compound represented by the following Chemical Formula 20, a chemical compound represented by the following Chemical Formula 21, or a combination thereof, and the chalcone-based photo-diamine may be a chemical compound represented by the following Chemical Formula 22. The coumarin-based photo-diamine may be a chemical compound represented by the following Chemical Formula 23.

[Chemical Formula 20]

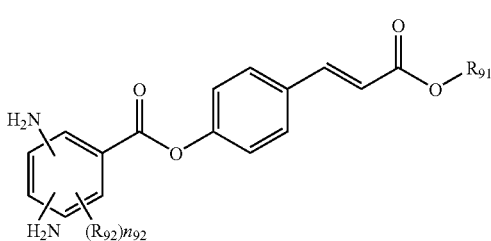

In the above Chemical Formula 20, $R_{91}$ is hydrogen, substituted or unsubstituted alkyl, substituted or unsubstituted aryl, or substituted or unsubstituted heteroaryl, each $R_{92}$ is substituted or unsubstituted alkyl, substituted or unsubstituted aryl, or substituted or unsubstituted heteroaryl, and $n_{92}$ is an integer ranging from 0 to 3.

[Chemical Formula 21]

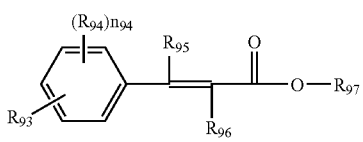

In the above Chemical Formula 21, $R_{97}$ is aromatic diamine, diamine including substituted or unsubstituted C2 to C24 linear or branched alkylene, or a combination thereof, wherein, in $R_{97}$, the substituted alkylene is alkylene substituted with halogen or cyano; alkylene including substituted or unsubstituted arylene, substituted or unsubstituted heteroarylene, substituted or unsubstituted cycloalkylene, substituted or unsubstituted heterocycloalkylene, —O—, —CO—, —CO—O—, —O—CO—, —Si(CH$_3$)$_2$—O—Si(CH$_3$)$_2$—, —NR'—, —NR'—CO—, —CO—NR'—, —NR'—CO—O—, —O—CO—NR'—, —CH=CH—, —C≡C—, or —O—CO—O— (wherein R' is hydrogen or substituted or unsubstituted C1 to C6 alkyl) instead of at least one of non-adjacent CH$_2$ group; or a combination thereof, each $R_{94}$ is substituted or unsubstituted C1 to C20 alkyl, substituted or unsubstituted C6 to C30 aryl, or substituted or unsubstituted C2 to C30 heteroaryl, and $n_{94}$ is an integer ranging from 0 to 4, $R_{95}$ and $R_{96}$ are independently hydrogen, halogen, cyano, or substituted or unsubstituted C1 to C12 alkyl, wherein, in $R_{95}$ and $R_{96}$, the substituted alkyl is alkyl substituted with heteroatom or cyano, alkyl including —O—, —CO—O—, —O—CO—, or —CH=CH— instead of at least one of non-adjacent CH$_2$ group, or a combination thereof, and $R_{93}$ is substituted or unsubstituted alkyl, substituted or unsubstituted alkylaryl, substituted or unsubstituted cycloalkyl, substituted or unsubstituted pyrimidinyl, substituted or unsubstituted pyridinyl, substituted or unsubstituted thiophenyl, substituted or unsubstituted furanyl, substituted or unsubstituted naphthyl, or substituted or unsubstituted phenyl, wherein, in $R_{93}$, the substituted alkyl is alkyl substituted with halogen or cyano, alkyl including —O—, —CO—O—, —O—CO—, or —CH=CH— instead of at least one non-adjacent CH$_2$ group, or a combination thereof, and the substituted alkylaryl is alkylaryl including —O—, —CO—O—, —O—CO—, or —CH=CH— instead of at least one of a non-adjacent CH$_2$ group.

[Chemical Formula 22]

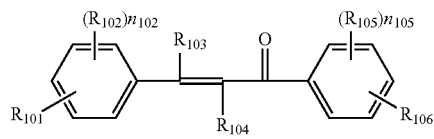

In the above Chemical Formula 22, $R_{101}$ is aromatic diamine, diamine including substituted or unsubstituted C2 to C24 linear or branched alkylene, or a combination thereof, wherein, in $R_{101}$, the substituted alkylene is alkylene substituted with halogen or cyano, alkylene including substituted or unsubstituted arylene, substituted or unsubstituted heteroarylene, substituted or unsubstituted cycloalkylene, substituted or unsubstituted heterocycloalkylene, —O—, —CO—, —CO—O—, —O—CO—, —Si(CH$_3$)$_2$—O—Si(CH$_3$)$_2$—, —NR'—, —NR'—CO—O—, —CO—NR'—, —NR'—CO—O—, —O—CO—NR'—, —CH=CH—, —C≡C—, or —O—CO—O— (wherein R' is hydrogen or substituted or unsubstituted C1 to C6 alkyl) instead of at least one of a non-adjacent CH$_2$ group, or a combination thereof, each $R_{102}$ and $R_{105}$ is independently substituted or unsubstituted C1 to C20 alkyl, substituted or unsubstituted aryl, or substituted or unsubstituted heteroaryl, and $n_{102}$ and $n_{105}$ are independently integers ranging from 0 to 4, $R_{103}$ and $R_{104}$ are independently hydrogen, halogen, cyano, or substituted or unsubstituted C1 to C12 alkyl, wherein, in $R_{103}$ and $R_{104}$, the substituted alkyl is alkyl substituted with halogen or cyano, alkyl including —O—, —CO—O—, —O—CO—, or —CH=CH— instead of at least one of non-adjacent CH$_2$ group, or a combination thereof, and $R_{105}$ is substituted or unsubstituted alkyl, substituted or unsubstituted alkylaryl, substituted or unsubstituted cycloalkyl, substituted or unsubstituted pyrimidinyl, substituted or unsubstituted pyridinyl, substituted or unsubstituted thiophenyl, substituted or unsubstituted furanyl, substituted or unsubstituted naphthyl, or substituted or unsubstituted phenyl, wherein, in $R_{106}$, the substituted alkyl is alkyl substituted with halogen or cyano, alkyl including —O—, —CO—O—, —O—CO—, or —CH=CH— instead of at least one of non-adjacent $CH_2$ group, or a combination thereof, and the substituted alkylaryl is alkylaryl including —O—, —CO—O—, —O—CO—, or —CH=CH— instead of at least one of a non-adjacent $CH_2$ group.

[Chemical Formula 23]

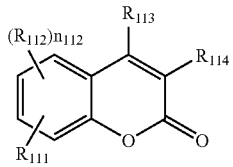

In the above Chemical Formula 23, $R_{111}$ is aromatic diamine, diamine including substituted or unsubstituted C2 to C24 linear or branched alkylene, or a combination thereof, wherein, in $R_{111}$, the substituted alkylene is alkylene substituted with halogen or cyano, alkylene including substituted or unsubstituted arylene, substituted or unsubstituted heteroarylene, substituted or unsubstituted cycloalkylene, substituted or unsubstituted heterocycloalkylene, —O—, —CO—, —CO—O—, —O—CO—, —Si(CH$_3$)$_2$—O—Si(CH$_3$)$_2$—, —NR'—, —NR'—CO—, —CO—NR'—, —NR'—CO—O—, —O—CO—NR'—, —CH=CH—, —C≡C—, or —O—CO—O— (wherein R' is hydrogen or substituted or unsubstituted C1 to C6 alkyl) instead of at least one of non-adjacent $CH_2$ group, or a combination thereof, each $R_{112}$ is substituted or unsubstituted C1 to C20 alkyl, substituted or unsubstituted aryl, or substituted or unsubstituted heteroaryl, and $n_{112}$ is an integer ranging from 0 to 4, and $R_{113}$ and $R_{114}$ are independently hydrogen, halogen, cyano, or substituted or unsubstituted C1 to C12 alkyl, wherein, in $R_{113}$ and $R_{114}$, the substituted alkyl is alkyl substituted with halogen or cyano, alkyl including —O—, —CO—O—, —O—CO—, or —CH=CH— instead of at least one of non-adjacent $CH_2$ group, or a combination thereof.

(D) Solvent

A liquid crystal photo-alignment agent according to an embodiment of the present invention includes a solvent.

The solvent may be any solvent that is capable of dissolving a polymer and an epoxy compound.

Exemplary solvents may include without limitation N-methyl-2-pyrrolidone, N,N-dimethyl acetamide, N,N-dimethyl formamide, dimethyl sulfoxide, γ-butyro lactone, phenol-based solvents such as meta cresol, phenol, or halgenated phenol, and the like, and combinations thereof.

Also, the solvent may further include a polar solvent, e.g., alcohols, ketones, esters, ethers, hydrocarbons, halgenated hydrocarbons, and the like, and combinations thereof, in an appropriate ratio as long as the polyimide polymer is not extracted. Polar solvents can decrease the surface energy of the liquid crystal photo-alignment agent so that the liquid crystal photo-alignment agent has excellent spread and flatness characteristics when it is applied to a substrate.

The liquid crystal photo-alignment agent may include the polar solvent in an amount ranging from about 1 to about 90 vol %, for example about 1 to about 70 vol %, based on the entire amount of solvent.

Non-limiting examples of the polar solvent include methanol, ethanol, isopropanol, cyclohexanol, ethylene glycol, propylene glycol, 1,4-butanediol, triethylene glycol, acetone, methylethylketone, cyclohexanone, methyl acetate, ethyl acetate, butyl acetate, diethyl hydroxide, malonic acid ester, diethyl ether, ethylene glycol monomethyl ether, ethylene glycol monoethyl ether, ethylene glycol phenyl ether, ethylene glycol phenyl methyl ether, ethylene glycol phenyl ethyl ether, ethylene glycol dimethylethyl, diethylene glycol dimethylethyl, diethylene glycol ether, diethylene glycol monomethyl ether, diethylene glycol monoethyl ether, diethylene glycol monomethyl ether acetate, diethylene glycol monoethyl ether acetate, ethylene glycol methyl ether acetate, ethylene glycol ethyl ether acetate, 4-hydroxy-4-methyl-2-pentanone, 2-hydroxy ethyl propionate, 2-hydroxy-2-methyl ethyl propionate, ethoxy ethyl acetate, hydroxy ethyl acetate, 2-hydroxy-3-methyl methyl butanoate, 3-methoxy methyl propionate, 3-methoxy ethyl propionate, 3-ethoxy ethyl propionate, 3-ethoxy methyl propionate, methyl methoxy butanol, ethyl methoxy butanol, methyl ethoxy butanol, ethyl ethoxy butanol, tetrahydrofuran, dichloromethane, 1,2-dichloroethane, 1,4-dichloro butane, trichloro ethane, chlorobenzene, o-dichlorobenzene, hexane, heptane, octane, benzene, toluene, xylene, and the like, and combinations thereof.

The amount of solvent is not limited in the liquid crystal photo-alignment agent, but according to one embodiment of the present invention, the solid content of the liquid crystal photo-alignment agent can range from about 1 to about 30 wt %. In another embodiment, the solid content of the liquid crystal photo-alignment agent can range from about 3 to about 15 wt %, and in a further embodiment, from about 5 to about 10 wt %. When the solid content is within the above ranges, the film may not be affected by the surface of the substrate so that the film uniformity and the transmittance are appropriately achieved due to the appropriate viscosity during the printing process.

The liquid crystal photo-alignment film according to another embodiment of the present invention is fabricated using the liquid crystal photo-alignment agent.

The liquid crystal photo-alignment agent is coated on a substrate to form a liquid crystal photo-alignment film. The liquid crystal photo-alignment agent can be coated using methods such as spin coating, flexo printing, inkjet printing, and the like. The flexo printing can accomplish excellent uniformity of a film and may easily form a larger liquid crystal photo-alignment film.

The substrate is not limited and may include a glass substrate or a plastic substrate such as an acryl substrate or a polycarbonate substrate, as long as it is transparent. In addition, the substrate can be a substrate including an ITO electrode and the like for liquid crystal operation in terms of simplifying a manufacturing process.

In order to improve film uniformity, the liquid crystal photo-alignment agent may be uniformly coated on a substrate and pre-dried at about room temperature to about 200° C., about 30 to about 150° C., or about 40 to about 120° C., for about 1 to about 100 minutes. The pre-drying can control volatility of each component of the liquid crystal photo-alignment agent, securing a uniform film without a thickness deviation.

Then, the coated substrate can be fired at a temperature of about 80 to about 300° C. or about 120 to about 280° C. for about 5 to about 300 minutes to completely evaporate the solvent, fabricating a liquid crystal photo-alignment film.

The liquid crystal photo-alignment film can be used for a liquid crystal display with uniaxial alignment treatment by polarized ultraviolet (UV) rays or rubbing, or without the uniaxial alignment treatment for some uses such as a vertical alignment film and the like.

The liquid crystal photo-alignment film according to an embodiment of the present invention may be exposed to energy ranging from about 10 mJ to about 5000 mJ for about 0.1 to about 180 minutes for uniaxial alignment treatment. Performing the uniaxial alignment treatment while reducing the photo-exposure intensity may completely remove double bonds included in the polyimide photo-polymer.

The following examples illustrate the present invention in more detail. These examples, however, should not in any sense be interpreted as limiting the scope of the present invention.

A person having ordinary skill in this art can sufficiently understand parts of the present invention that are not specifically described.

Preparation Example 1

Preparation of Epoxy Compound

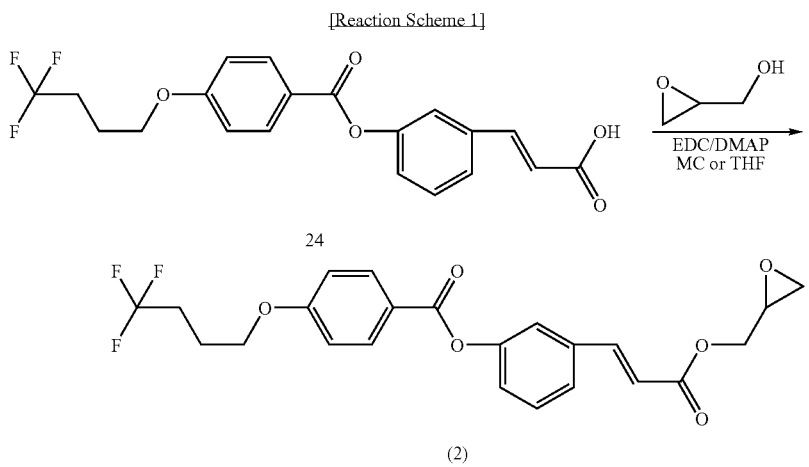

[Reaction Scheme 1]

(2)

An epoxy compound is prepared according to a method shown in Reaction Scheme 1.

1 equivalent of the compound 24 is dissolved in methylene chloride, and agitated at room temperature. 1 equivalent of glysidol, 1 equivalent of 1-ethyl-3-(3-dimethylaminopropyl) carbodiimide) (EDC) dissolved in HCl, and 1.2 equivalents of 3-dimethylamino propylamine (DMAP) are added to the solution and agitated for 16 hours.

The end of the reaction is confirmed by thin film chromatography (which uses a diffusion solvent including hexane and ethyl acetate at a volume ratio of 2:1), and the reaction solution is concentrated.

The concentrate reaction solution is suspended by ethyl acetate, and filtrated through a silica gel pad to thereby remove base and inorganic materials. The acquired filtrate is concentrated, and the concentrated solution is purified using a silica gel column and a diffusion solvent prepared by mixing hexane, methylene chloride, and ethyl acetate at a volume ratio of 1:1:0.5 to thereby produce a purified product. The purified product is concentrated, and the concentrated residue is rinsed with ethyl alcohol by suspending and agitating the concentrated residue in the presence of ethyl alcohol, and filtrated and dried to thereby prepare an epoxy compound represented by Chemical Formula 2.

$^1$H NMR of the epoxy compound is measured and is shown in FIG. 1.

Figure 2:
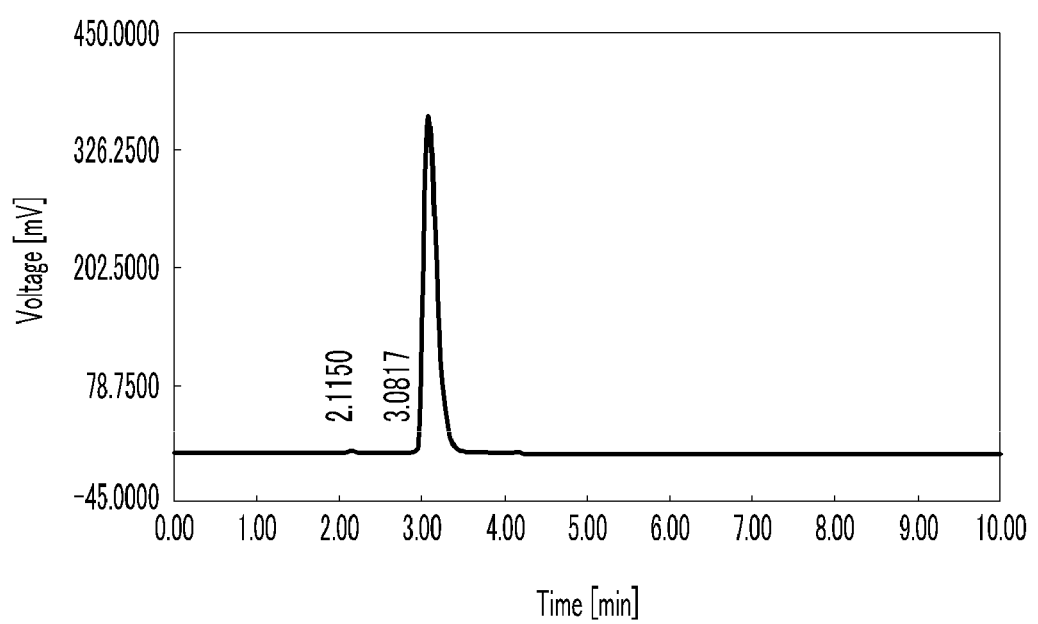
FIG. 2 is a graph showing results of high performance liquid chromatography (HPLC) of an epoxy compound prepared according to Example 1 of the present invention.

Also, the purity of the prepared epoxy compound is measured using high performance liquid chromatography (HPLC) and shown in FIG. 2. FIG. 2 shows only a peak corresponding to a target product, which confirms that the target product is acquired at a high purity with almost no impurities.

Preparation Example 2

Preparation of Polyamic Acid (PAA-1)

A mixed solution is prepared by passing nitrogen through a 4-neck flask connected to an agitator, a temperature controller, a nitrogen gas implanter, and a cooler, and adding 0.9 mol of paraphenylene diamine, 0.1 mol of functional diamine 3,5-diaminophenyldecyl succinimide represented by the following Chemical Formula 25, and N-methyl-2-pyrrolidone (NMP).

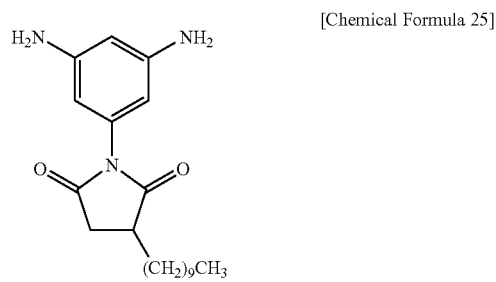

[Chemical Formula 25]

1.0 mol of solid-state 1,2,3,4-cyclobutane tetracarboxylic acid dianhydride is added to the mixed solution and agitated vigorously. The content of the solid is 20 wt %, and the temperature is maintained in a range between 30° C. and 50° C. for 10 hours for reaction to thereby prepare a polyamic acid resin. A mixed organic solvent of N-methyl-2-pyrrolidone and γ-butyrolactone is added to the prepared polyamic acid resin, and the mixed solution is agitated at room temperature for 24 hours to thereby prepare a polyamic acid solution (PAA-1) including 6 wt % of the solid.

Preparation Example 3

Preparation of Polyimide Polymer (SPI-1)

A mixed solution is prepared by passing nitrogen through a 4-neck flask connected to an agitator, a temperature controller, a nitrogen gas implanter, and a cooler, and adding 0.8 mols of phenylene diamine, 0.2 mols of diamine 3,5-diaminophenyldecyl succinimide represented by Chemical Formula 25, and N-methyl-2-pyrrolidone.

A polyamic acid solution (PAA-2) is prepared according to the same method as Preparation Example 1, except that 4,10-dioxa-tricyclo[6.3.1.02,7]dodecane-3,5,9,11-tetraone is used instead of 1.0 mol of solid-state 1,2,3,4-cyclobutane tetracarboxylic acid dianhydride for the mixed solution. The content of the solid is 20 wt %, and the polyamic acid solution is prepared by maintaining the temperature in a range between 30° C. and 50° C. for 10 hours for the reaction.

A soluble polyimide resin is prepared by adding 3.0 mol of acetic acidanhydride and 5.0 mol of pyridine to the prepared polyamic acid solution, raising the temperature to 80° C., causing a reaction for 6 hours, and removing the catalyst and solvent through vacuum distillation.

A polyimide solution (SPI-1) including 6 wt % of solid is prepared by adding a mixed organic solvent of N-methyl-2-pyrrolidone and γ-butyrolactone to the prepared soluble polyimide resin, and agitating the solution at room temperature for 24 hours.

Preparation of Liquid Crystal Photo-Alignment Agent

Example 1

A polymer solution is prepared by adding 20 g of the SPI-1 solution including 6 wt % of the solid acquired from Preparation Example 3 to 80 g of the PAA-1 solution including 6 wt % of the solid acquired from Preparation Example 2. A liquid crystal photo-alignment agent (referred to as PSPI-1 hereafter) including 6 wt % of a solid is acquired by adding an epoxy compound prepared in Preparation Example 1 to the polymer solution, agitating the solution for 24 hours while passing nitrogen therethrough, and filtrating the solution with a filter having a particle diameter of 0.1 μm. The amount of the epoxy compound used is 6 parts by weight based on 100 parts by weight of the entire solids of the PAA-1 solution, the SPI-1 solution, and the epoxy compound.

Example 2

A liquid crystal photo-alignment agent including 6 wt % of a solid (referred to as PSPI-2 hereafter) is acquired according to the same method as Example 1, except that the used amount of the epoxy compound is changed to 10 parts by weight based on 100 parts by weight of the entire solids of the PAA-1 solution, the SPI-1 solution, and the epoxy compound.

Example 3

A liquid crystal photo-alignment agent including 6 wt % of a solid (referred to as PSPI-3 hereafter) is acquired according to the same method as Example 1, except that the amount of the epoxy compound used is changed to 20 parts by weight based on 100 parts by weight of the entire solids of the PAA-1 solution, the SPI-1 solution and the epoxy compound.

Example 4

A liquid crystal photo-alignment agent including 6 wt % of a solid (referred to as PSPI-4 hereafter) is acquired according to the same method as Example 1, except that the amount of the epoxy compound used is changed to 8 parts by weight based on 100 parts by weight of the entire solids of the PAA-1 solution, the SPI-1 solution and the epoxy compound.

Example 5

A liquid crystal photo-alignment agent including 6 wt % of a solid (referred to as PSPI-5 hereafter) is acquired according to the same method as Example 1, except that the amount of the epoxy compound used is changed to 12 parts by weight based on 100 parts by weight of the entire solids of the PAA-1 solution, the SPI-1 solution and the epoxy compound.

Example 6

A liquid crystal photo-alignment agent including 6 wt % of a solid (referred to as PSPI-6 hereafter) is acquired according to the same method as Example 1, except that the amount of the epoxy compound used is changed to 15 parts by weight based on 100 parts by weight of the entire solids of the PAA-1 solution, the SPI-1 solution and the epoxy compound.

Example 7

A liquid crystal photo-alignment agent including 6 wt % of a solid (referred to as PSPI-8 hereafter) is acquired according to the same method as Example 1, except that the amount of the epoxy compound used is changed to 25 parts by weight based on 100 parts by weight of the entire solids of the PAA-1 solution, the SPI-1 solution and the epoxy compound.

Example 8

A liquid crystal photo-alignment agent including 6 wt % of a solid (referred to as PSPI-8 hereafter) is acquired according to the same method as Example 1, except that the amount of the epoxy compound used is changed to 30 parts by weight based on 100 parts by weight of the entire solids of the PAA-1 solution, the SPI-1 solution and the epoxy compound.

Comparative Example 1

A liquid crystal photo-alignment agent including 6 wt % of a solid (referred to as PSPI-10) is acquired by agitating 100 g of the PAA-1 solution including 6 wt % of the solid acquired from Preparation Example 2 for 24 hours while passing nitrogen therethrough and filtrating the solution with a filter having a particle diameter of 0.1 μm.

Comparative Example 2

A liquid crystal photo-alignment agent including 6 wt % of a solid (referred to as PSPI-11) is acquired by agitating 100 g of the SPI-1 solution including 6 wt % of the solid acquired from Preparation Example 3 for 24 hours while passing nitrogen therethrough and filtrating the solution with a filter having a particle diameter of 0.1 μm.

Comparative Example 3

A liquid crystal photo-alignment agent including 6 wt % of a solid (referred to as PSPI-12) is acquired by adding 20 g of SPI-1 solution including 6 wt % of the solid acquired from Preparation Example 3 to 80 g of the PAA-1 solution including 6 wt % of the solid acquired from Preparation Example 2, agitating the mixed solution for 24 hours while passing nitrogen therethrough, and filtrating the solution with a filter having a particle diameter of 0.1 μm.

Evaluation of Printability and End Film Uniformity

The liquid crystal photo-alignment agents prepared according to Examples 1 to 8 and Comparative Examples 1 to 3 are flexo-printed on rinsed glass substrates with ITO attached thereto by using an alignment film printer (CZ 200® Nakan Company). The printed substrates are maintained in a hot plate at a temperature of 50 to 90° C. for 2 to 5 minutes for pre-drying of the film.

After the substrates are pre-dried, the substrates are baked in the hot plate at a temperature ranging from 200 to 230° C. for 10 to 30 minutes, and exposed to energy ranging from 10 mJ to 5000 mJ for 0.1 to 180 minutes to thereby prepare substrates with a liquid crystal photo-alignment film attached thereto.

The film surfaces of the liquid crystal photo-alignment films are observed with bare eyes and an electron microscope (MX50® Olympus Company), and printability, such as pinholes and stains, and variations in the thickness of the photo-alignment films, are measured across the substrates including the central part and edges of the substrates. The results are as shown in the following Table 1.

In the following Table 1, printability is marked as "good" when the number of pinholes is 0 to 3, marked as "normal" when the number of pinholes is 3 to 5, and marked as "poor" when the number of pinholes is 6 or more. Stain is marked as "good" when no stain appeared, and marked as "poor" when there is a stain appearing. Film uniformity is marked as "good" when the thickness deviation is less than 0.005 μm, marked as "normal" when the thickness deviation is between 0.005 and 0.01 μm, and marked as "poor" when the thickness deviation exceeds 0.01 μm.

(Liquid Crystal Orientation of Liquid Crystal Photo-Alignment Film)

A liquid crystal cell is manufactured to measure the liquid crystal orientation property of the liquid crystal photo-alignment agent. The liquid crystal cell is manufactured as follows.

A standardized ITO glass substrate is patterned by a photolithography process to remove parts of the ITO other than an area of a 1.5 cm×1.5 cm square ITO and an electrode ITO for applying a voltage thereto.

Each of the liquid crystal agents obtained from Examples 1 to 8 and Comparative Examples 1 and 2 is applied and spin-coated on the patterned ITO substrate to provide a 0.1 μm thickness, and is then cured at 70° C. and 210° C.

The cured ITO substrate is exposed with an exposer UIS-S2021J7-YD01, Ushio LPUV) at a certain angle and under a certain energy. Two such substrates are placed opposite to each other so that the exposed directions are opposite (VA mode, 90 degree), and are bonded so that the square ITO shapes are identical to each other while maintaining the cell gap of 4.75 μm. During the exposure process, the light source is a 2 kW deep UV lamp (deep UV lamp, UXM-2000).

The obtained cell is filled with liquid crystal, and then the liquid crystal orientation property is observed with a perpendicularly polarized optical microscope. The results are shown in the following Table 1.

(Electrical Characteristic and Optical Characteristic of Liquid Crystal Photo-Alignment Film)

The electrical and optical characteristics of the liquid crystal photo-alignment films are determined by measuring voltage-transmission curve, voltage holding ratio, and residual DC voltage with a liquid crystal cell having a cell gap of 4.75 μm.

The electrical and optical characteristics such as voltage-transmission curve, voltage holding ratio, and residual DC voltage are summarized as follows.

The voltage-transmission curve is one of the important electrical and optical characteristics, and one determining the driving voltage for a LCD. This is a standardized curve by considering the quantity of light of the brightest state as 100% and the quantity of light of the darkest state as 0% when a voltage is applied to the liquid crystal cell for measuring the transmission.

The voltage holding ratio is determined as a degree at which the floating liquid crystal layer (with the external electrical source) maintains the charged voltage for an unselected period in an active matrix TFT-LCD. The value is more ideal as it approaches 100%.

The residual DC voltage indicates a voltage that is applied to the liquid crystal layer when the external voltage is not applied, due to the ionized impurities of the liquid crystal layer that are absorbed on the alignment film. The value is more ideal as it becomes lower. Common methods of measuring the residual DC voltage include a method using flicker and a method using an electrical capacity change curve (C-V) of the liquid crystal layer depending upon the DC voltage.

The results of the electrical and optical characteristics of the liquid crystal photo-alignment films using the liquid crystal cell are shown in the following Table 1.

TABLE 1

| Sample | Printability | Film uniformity | Photo-alignment property | Voltage-transmission | Voltage holding ratio (%) Room temp. (60 Hz) | Voltage holding ratio (%) Room temp. (10 Hz) | Residual DC (by C-V) |
|---|---|---|---|---|---|---|---|
| Example 1 | Good | Good | Good | Good | 99.42 | 98.15 | 142 |
| Example 2 | Good | Good | Good | Good | 99.25 | 98.12 | 138 |
| Example 3 | Good | Good | Good | Good | 99.22 | 98.23 | 154 |
| Example 4 | Good | Good | Good | Good | 99.52 | 98.26 | 106 |
| Example 5 | Good | Good | Good | Good | 99.48 | 98.18 | 72 |
| Example 6 | Good | Good | Good | Good | 99.56 | 99.16 | 83 |

TABLE 1-continued

| Sample | Printability | Film uniformity | Photo-alignment property | Voltage-transmission | Voltage holding ratio (%) Room temp. (60 Hz) | Room temp. (10 Hz) | Residual DC (by C-V) |
|---|---|---|---|---|---|---|---|
| Example 7 | Good | Good | Good | Good | 99.59 | 99.15 | 69 |
| Example 8 | Good | Good | Good | Good | 99.67 | 99.12 | 72 |
| Comparative Example 1 | Good | Good | Poor | Good | 98.52 | 92.11 | 365 |
| Comparative Example 2 | Good | Good | Poor | Good | 98.48 | 94.30 | 480 |
| Comparative Example 3 | Good | Good | Poor | Good | 98.51 | 92.23 | 652 |

Table 1 shows that the liquid crystal photo-alignment agents of Examples 1 to 8 have excellent printability, film uniformity, voltage-transmission, voltage holding ratio, and residual DC characteristics.

The voltage holding ratio and the residual DC are references for determining the after-image characteristics of the liquid crystal photo-alignment films. They have increasingly better after-image characteristics as the voltage holding ratio is increased and the residual DC is decreased. Accordingly, it is understood that the liquid crystal photo-alignment agents according to Examples 1 to 8 have much better after-image characteristics than the liquid crystal photo-alignment agents according to Comparative Examples 1 to 3.

Many modifications and other embodiments of the invention will come to mind to one skilled in the art to which this invention pertains having the benefit of the teachings presented in the foregoing description. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation, the scope of the invention being defined in the claims.

What is claimed is:

1. An epoxy compound for a liquid crystal photo-alignment agent represented by the following Chemical Formula 1:

[Chemical Formula 1]

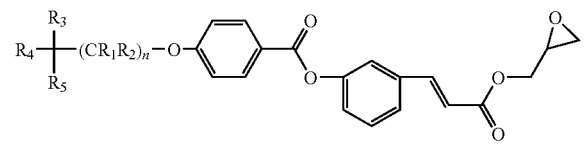

wherein in the above Chemical Formula 1,
each $R_1$ and $R_2$ is independently hydrogen or substituted or unsubstituted alkyl,
$R_3$, $R_4$, and $R_5$ are independently hydrogen, halogen, or substituted or unsubstituted alkyl, and
n ranges from 1 to 20.

2. The epoxy compound of claim 1, wherein each $R_1$ and $R_2$ is independently hydrogen, $R_3$, $R_4$, and $R_5$ are independently halogen, and n is 2, 3, or 4.

3. The epoxy compound of claim 1, wherein the epoxy compound comprises at least one compound represented by the following Chemical Formulae 2 and 3:

[Chemical Formula 2]

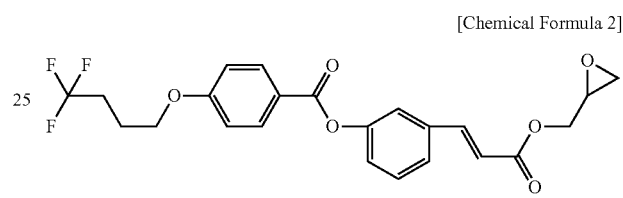

[Chemical Formula 3]

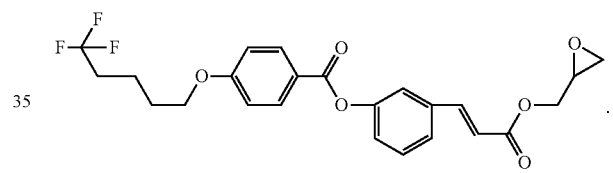

4. A liquid crystal photo-alignment agent comprising:
an epoxy compound represented by the following Chemical Formula 1

[Chemical Formula 1]

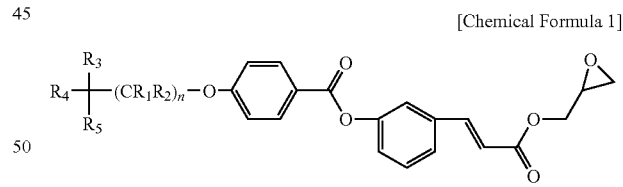

wherein, in the above Chemical Formula 1,
each $R_1$ and $R_2$ is independently hydrogen or substituted or unsubstituted alkyl,
$R_3$, $R_4$, and $R_5$ are independently hydrogen, halogen, or substituted or unsubstituted alkyl, and
n ranges from 1 to 20; and
a polymer of polyamic acid, a polyimide polymer, or a combination thereof.

5. The liquid crystal photo-alignment agent of claim 4, comprising the epoxy compound in an amount of about 0.01 to about 60 parts by weight based on about 100 parts by weight of the epoxy compound and the polymer.

6. The liquid crystal photo-alignment agent of claim 4, wherein the epoxy compound comprises at least one compound represented by the following Chemical Formulae 2 and 3:

[Chemical Formula 2]

[Chemical Formula 3]

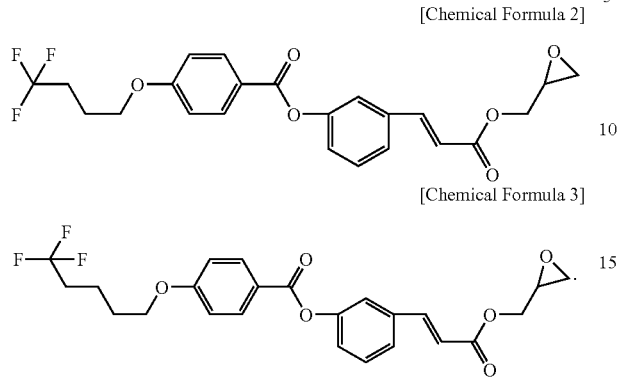

7. The liquid crystal photo-alignment agent of claim 4, wherein the polyamic acid is represented by the following Chemical Formula 5:

[Chemical Formula 5]

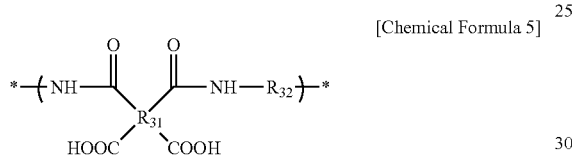

wherein, in the above Chemical Formula 5,
$R_{31}$ is a quadrivalent organic group derived from an aliphatic cyclic acid dianhydride or an aromatic acid dianhydride, and
$R_{32}$ is a divalent organic group derived from a diamine.

8. The liquid crystal photo-alignment agent of claim 4, wherein the polyimide polymer is represented by the following Chemical Formula 6:

[Chemical Formula 6]

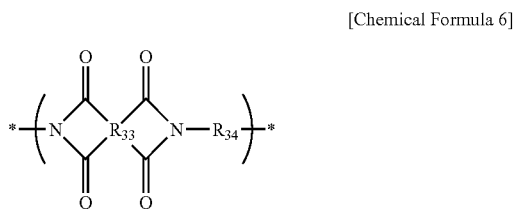

wherein, in the above Chemical Formula 6,
$R_{33}$ is an quadrivalent organic group derived from an aliphatic cyclic acid dianhydride or an aromatic acid dianhydride, and
$R_{34}$ is a divalent organic group derived from an aromatic diamine or a divalent organic group derived from a cumarin-based photodiamine, a chalcone-based photodiamine, or a cinnamate-based photodiamine.

9. A liquid crystal photo-alignment film fabricated by applying the liquid crystal photo-alignment agent according to claim 4.

* * * * *